United States Patent
Egami et al.

(10) Patent No.: US 8,533,007 B2
(45) Date of Patent: Sep. 10, 2013

(54) CHRONIC ILLNESS GOAL MANAGEMENT

(75) Inventors: Tadashi Egami, Belmont, CA (US); John C. Ryan, Boston, MA (US)

(73) Assignee: Koninklijke Philips N.V., Eindhoven (NL)

(*) Notice: Subject to any disclaimer, the term of this patent is extended or adjusted under 35 U.S.C. 154(b) by 707 days.

(21) Appl. No.: 12/096,081

(22) PCT Filed: Dec. 5, 2006

(86) PCT No.: PCT/IB2006/054600
§ 371 (c)(1),
(2), (4) Date: Jun. 4, 2008

(87) PCT Pub. No.: WO2007/066284
PCT Pub. Date: Jun. 14, 2007

(65) Prior Publication Data
US 2008/0319797 A1 Dec. 25, 2008

Related U.S. Application Data

(60) Provisional application No. 60/742,239, filed on Dec. 5, 2005.

(51) Int. Cl.
*G06Q 10/00* (2012.01)

(52) U.S. Cl.
USPC .................................. 705/3; 705/2

(58) Field of Classification Search
USPC ............................................. 705/3
See application file for complete search history.

(56) References Cited

U.S. PATENT DOCUMENTS

| | | | |
|---|---|---|---|
| 6,039,688 A | 3/2000 | Douglas et al. | |
| 6,997,852 B2* | 2/2006 | Watterson et al. | 482/1 |
| 2002/0055859 A1* | 5/2002 | Goodman et al. | 705/3 |
| 2002/0187463 A1 | 12/2002 | Aspe et al. | |
| 2003/0022141 A1 | 1/2003 | Packard | |
| 2004/0010420 A1* | 1/2004 | Rooks | 705/2 |
| 2004/0133079 A1* | 7/2004 | Mazar et al. | 600/300 |
| 2004/0219500 A1 | 11/2004 | Brown et al. | |
| 2005/0021372 A1 | 1/2005 | Mikkelsen et al. | |
| 2005/0060187 A1 | 3/2005 | Gottesman | |

FOREIGN PATENT DOCUMENTS

| | | |
|---|---|---|
| JP | 2004133669 A | 4/2004 |
| WO | 01/77665 A2 | 10/2001 |

OTHER PUBLICATIONS

Ouwens et all, "Integrated Care Programmes for Chronically Ill Patients: A Review of Systematic Reviews", International Journal for Quality in Health Care, vol. 17, No. 2, Jan. 21, 2005, pp. 141-146.

D.A. Leiberman, "Designing Interactive Video Games for Children's Health Education", Interactive Technology and the New Paradigm for Healthcare, Abstract, 1995.

* cited by examiner

*Primary Examiner* — Hiep V Nguyen

(57) ABSTRACT

A health management system includes a plurality of goal modules (14). Each goal module includes one or more content sessions (16, 18, 71, 72, 73, 74, 120, 122, 126, 140, 148) cooperatively directed toward achieving a health management goal. A user interface (30) is configured for presenting content sessions. At least one feedback path (30, 32, 36, 38) provides at least one input indicative of a user response to a content session presented by the user interface. A content flow engine (42) is configured to control an order of presentation of content sessions based on the at least one input and on content flow rules (44, 46, 48).

10 Claims, 6 Drawing Sheets

CHRONIC ILLNESS GOAL MANAGEMENT

Figure 1:
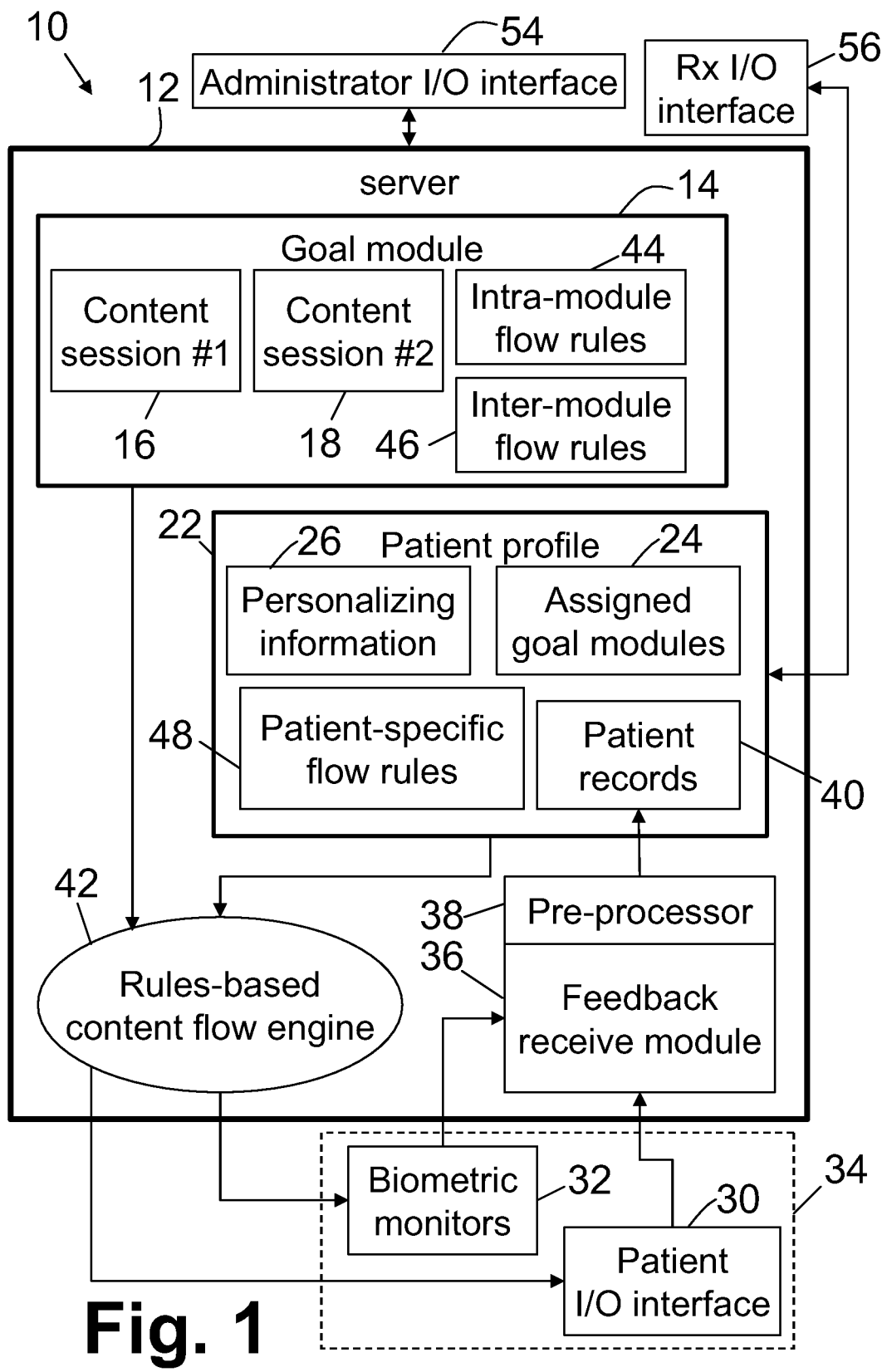

The following relates to the health management arts. It finds particular application in conjunction with out-patient management of chronic illnesses such as congestive heart failure, emphysema, chronic obstructive pulmonary disease (COPD), and so forth, and will be described with particular reference thereto. It finds application more generally in conjunction with methods and apparatuses for providing extended-term health management for: chronic diseases; rehabilitation from a catastrophic event such as a stroke or an automobile accident; managing weight; controlling insomnia; redressing health-impacting lifestyle issues such as smoking or poor diet or inadequate physical exercise; avoiding potential medical conditions such as osteoporosis or tooth decay; general chronic care such as general medication management or life planning for advance directives; and so forth.

Existing medical interventional paradigms are typically event-oriented. For example, a patient suffers a heart attack, stroke, automobile accident, or other catastrophic medical event. The patient is hospitalized, medical personnel obtain a rapid diagnosis of the condition and provide rapid remedial care such as surgery, administration of prescription medications, or so forth. As another example, a chronic illness such as heart failure is diagnosed during a routine medical check-up or other non-emergency visit the physician's office. The person is admitted to the hospital. Intensive in-patient monitoring and diagnostic tests are performed to clarify the diagnosis, and rapid in-patient remedial care is provided.

Rapid-response, event-oriented medical intervention is important. However, subsequent extended-term health management is also important in achieving the full medical recovery and re-attaining a high quality of life. Extended term health management or chronic care is typically performed on an out-patient basis, and is typically wholly or in large part self-administered.

Existing medical interventional paradigms are less effective at ensuring successful extended term health management, such as timely intake of medications, maintenance of a prescribed diet or exercise regimen, lifestyle modifications such as quitting smoking, or so forth. This is due to a lack of resources on the clinical side and in many cases lack of patient engagement in their own self-care.

For example, the patient who is admitted to the hospital after a heart attack, stroke, diagnosed heart failure, or so forth, typically undergoes a relatively short hospital stay of a few days to a few weeks. When discharged from the hospital, the patient is deluged with information on how to manage the condition in the extended term. For example, the discharged patient is typically prescribed a number of medications which while in the hospital had been timely administered by nurses. After discharge, however, the person must manage self-administration of these medications on a timely basis. Similarly, in-patient diet and exercise, which had been dictated by nurses, dieticians, therapists, or other hospital personnel, become the patient's responsibility immediately upon discharge from the hospital.

To assist the patient in making the transition from hospital-provided care to self-care, the discharge process typically includes rapid-fire sessions with, for example: a nurse who goes over the prescribed medications; a dietician who explains prescribed dietary restrictions or requirements; and a rehabilitation therapist who goes over a prescribed exercise regimen. The patient may also be given pamphlets or other printed material explaining this subject matter. After discharge, however, the patient is left on his or her own, except perhaps for an occasional follow-up visit with the physician, infrequent rehabilitation therapy sessions, or so forth. Without an ability for the physician to track patient behavior, the de facto assumption is that the patient has all they need in terms of self-care, but this has proven sadly not to be the case in many instances.

In summary, the discharged patient, who is typically in a weakened physical state, is overwhelmed with a deluge of rapidly provided information, and is thereafter provided with limited or no follow-up support. With such limited assistance, it is not surprising that recovering patients sometimes fall short in efforts to follow a prescribed extended-term health management program. Patients may fail to administer medicines properly or in a timely fashion, or may fail to follow prescribed dietary and exercise regimens. These failures may be caused by a lack of understanding of the health management program on the part of the patient.

Failures to follow the health management program may also be caused by apathy or lack of motivation, fear of failure, or other mental aspects on the part of the patient. While in the hospital, the patient receives frequent reassurances from nurses and other hospital personnel that the patient's condition is being treated. Measurable improvements in the patient's condition are typically noted by nurses or visiting doctors, and the patient looks forward to discharge from the hospital as definitive evidence of substantial recovery.

After discharge, however, such positive feedback and encouragement typically abruptly ceases. At precisely the time when the person must take over the extended-term health management, the person receives little or no feedback as to whether the condition is improving, remaining steady, or relapsing. Under these conditions, the patient may be unmotivated to follow medicine dosage schedules, dietary restrictions or requirements, or exercise regimens. Failure to follow these health management protocols, in turn, leads to less than complete recovery or even can cause relapse of the condition that led to the initial hospitalization.

Various techniques have been developed to support the patient in executing the extended term health maintenance program. For example, patients are sometimes afforded the opportunity to enroll in on-site rehabilitation therapy programs, in which the patient visits the hospital or other medical facility as an out-patient on a weekly basis or at other time intervals to engage in rehabilitative therapy. However, on-site therapy programs suffer from certain deficiencies. Because the sessions occur at infrequent intervals, the patient is not provided with daily encouragement and feedback. Moreover, on-site therapy programs are typically group programs. Accordingly, the therapy program is not tailored to the specific needs of the patient. Improved patient-specificity can be achieved by using smaller groups or one-on-one sessions. However, small groups or one-on-one sessions can be prohibitively expensive in terms of money and time. Furthermore, patients suffering from chronic illness are sometimes relatively immobile or even house-bound, and therefore cannot readily take advantage of on-site therapy programs. Even for such serious conditions as heart failure, it is estimated that only 10-20% of patients prescribed such rehabilitation programs actually attend.

Another approach for assisting extended term health management is the use of pre-recorded content. For example, the patient can be provided with an instructional or exercise video. The patient can use the video whenever convenient, and can replay the video as needed. However, pre-recorded content as presently provided has certain deficiencies. Typical videos or other pre-recorded content do not generally allow for substantive patient feedback. At most, a patient may fill out a questionnaire or survey and return this to the provider of the video. Such a survey may assist the provider in improving the video product, but does little to assist the person who fills out the survey.

Existing pre-recorded content is also typically not tailored to the specific needs of the patient. Most pre-recorded content targets a broad class of patients, such as all patients suffering heart failure. Within this class, however, different patients may have different goals. Some patients may need to stop smoking, while others may be non-smokers. Some patients may need to lose weight, while others do not. Younger patients may be suited for a more aggressive exercise regimen than older patients. On the other hand, as the specificity of the video increases (for example, by producing a video aimed at older, overweight, non-smoking heart failure patients), the group size of the class becomes smaller, increasing the cost-per-patient of the video.

Pre-recorded content is also typically not responsive to the level of learning or comprehension ability of the patient. Some patients may grasp the concepts being taught by the video quickly, while others may need reinforcement or remedial training. Existing videos can be replayed in their entirety by the person viewing the video; however, it may be difficult to replay only a selected portion of the video. Moreover, the patient may be unaware of which portions of the video the patient failed to understand (or misunderstood), or the patient may lack motivation to replay the video.

The following contemplates improvements that overcome the aforementioned limitations and others.

According to one aspect, a health management system is disclosed. A plurality of goal modules are provided. Each goal module includes one or more content sessions cooperatively directed toward achieving a health management goal. A user interface is configured for presenting content sessions. At least one feedback path provides at least one input indicative of a user response to a content session presented by the user interface. A content flow engine is configured to control an order of presentation of content sessions based on the at least one input and on content flow rules.

According to another aspect, a health management system is disclosed. A server communicates with a plurality of patients. The server stores at least: a plurality of goal modules, each goal module including one or more content sessions cooperatively directed toward achieving a health management goal; and a plurality of patient profiles corresponding to the plurality of patients, each patient profile indicating at least which goal module or goal modules are assigned to the patient profiled by that patient profile. The server further includes a content flow engine configured to control an order of presentation of content sessions to each patient based on at least one input from the patient and on content flow rules.

According to another aspect, a health management method is disclosed. A plurality of goal modules are provided. Each goal module includes one or more content sessions cooperatively directed toward achieving a health management goal. A first content session is presented. At least one input is received that is indicative of a user response to presented first content session. A second content session is selected based on user response and on content flow rules. The second content session is presented.

One advantage resides in providing more personalized health management assistance without corresponding increase in time commitment by medical personnel.

Another advantage resides in frequent (such as daily) feedback to an out-patient regarding the status or progress of his or her health management.

Another advantage resides in more reliable transfer of health management information to out-patients.

Another advantage resides in providing the clinician with insight into a patient's behavior or actions, awareness (for example, from testing of content material by quizzes or so forth) and attitude (for example, from self-reporting of motivation or confidence towards a particular goal). The clinician advantageously gains such insights without engaging in lengthy discussions. This represents upfront efficiency, and also provides an opportunity for increased efficacy by being able to quickly identify critical stumbling blocks or issues that the patient has in their overall care protocol.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

FIG. 1 diagrammatically shows principal components of an example health management system.

Figure 2:
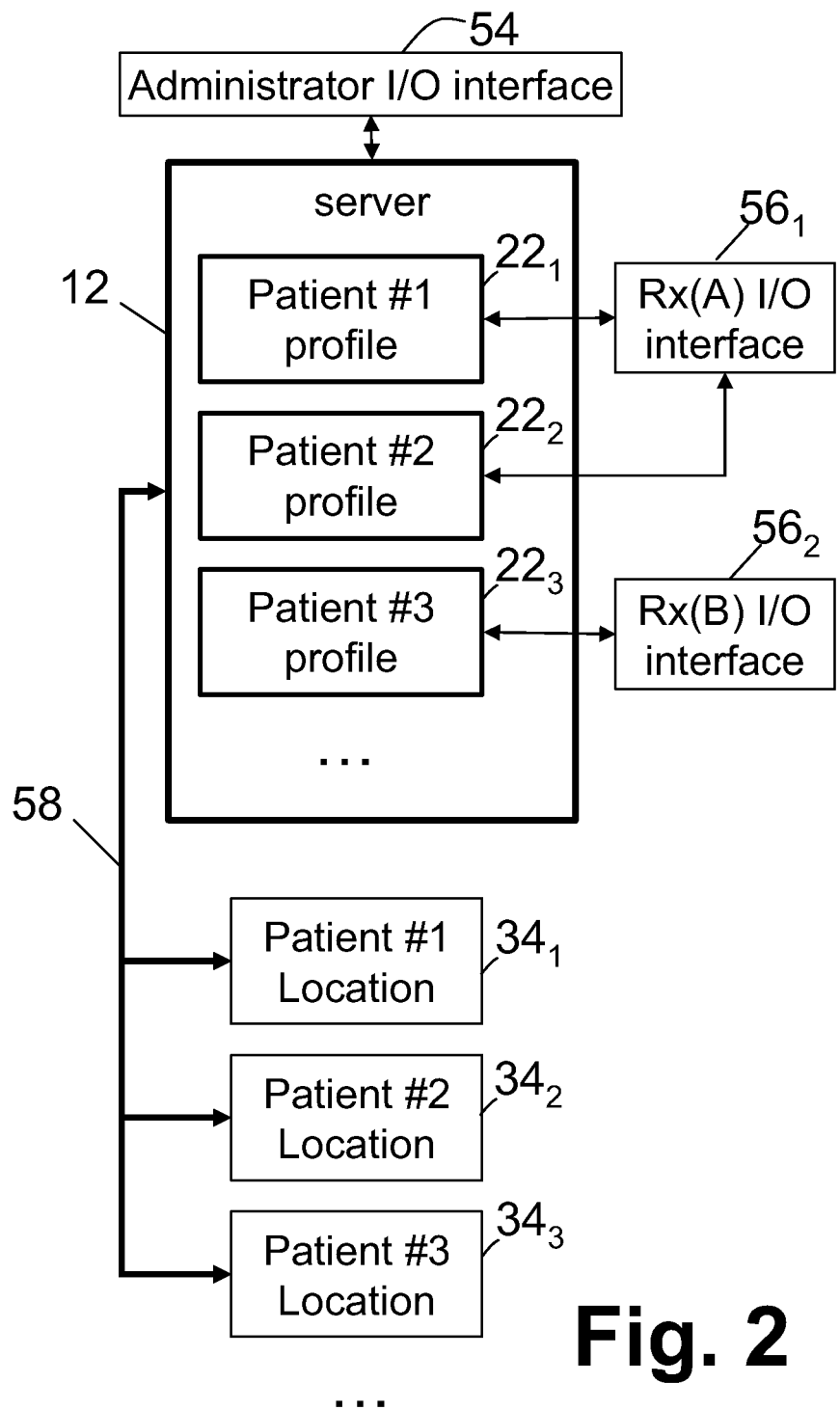

FIG. 2 diagrammatically shows a suitable relatively centralized arrangement of components of the health management system of FIG. 1.

Figure 3:
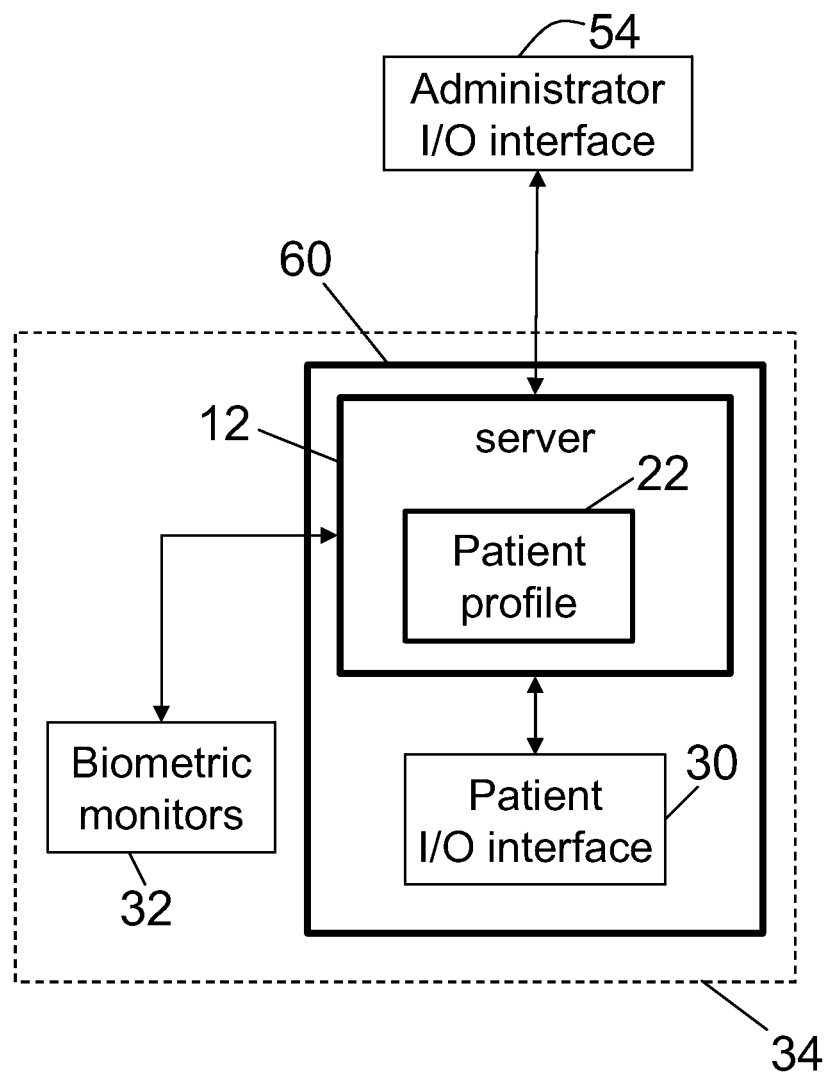

FIG. 3 diagrammatically shows a suitable relatively decentralized arrangement of components of the health management system of FIG. 1.

Figure 4:
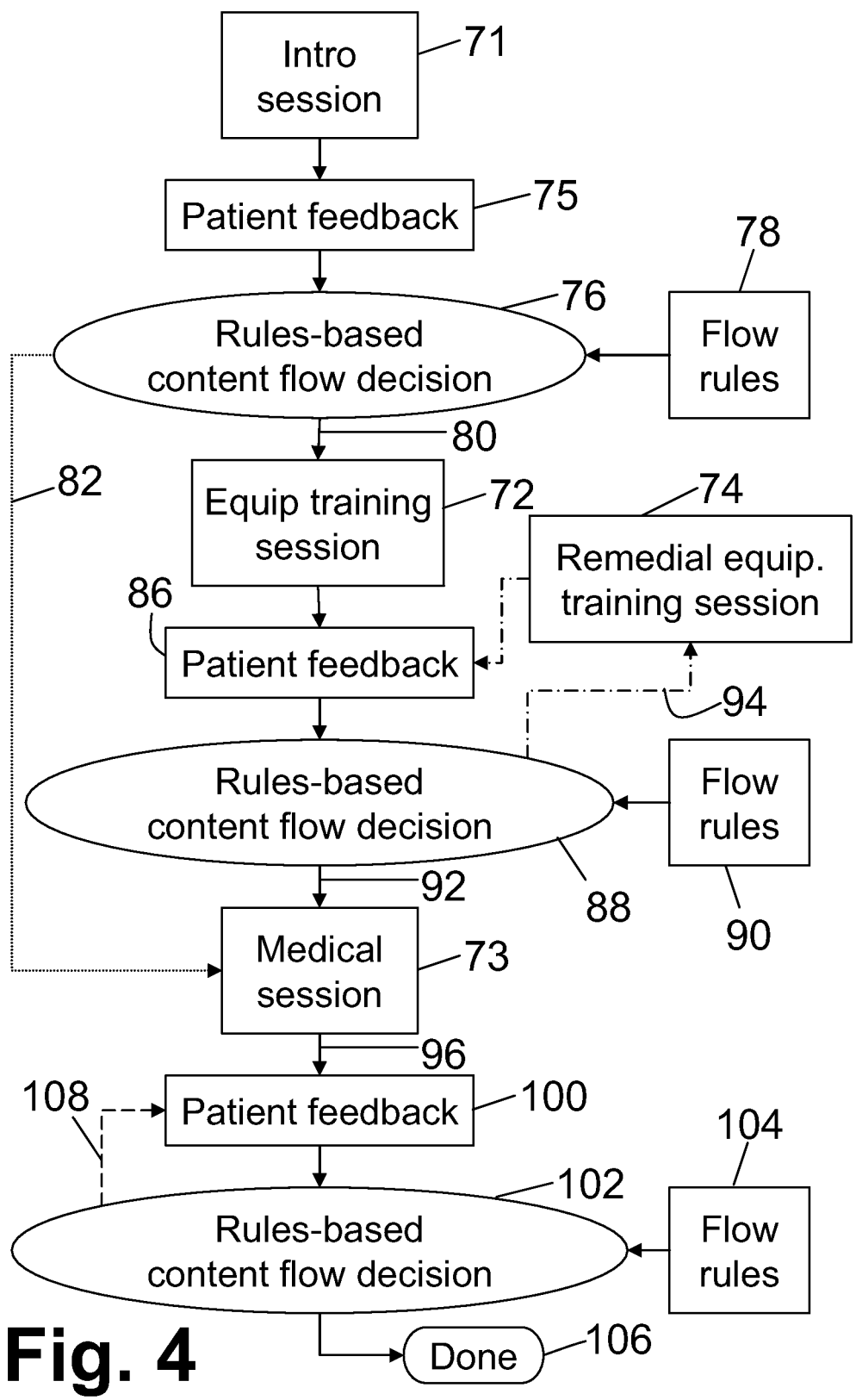

FIG. 4 diagrammatically shows some potential pathways for content flow in a typical goal module.

Figure 5:
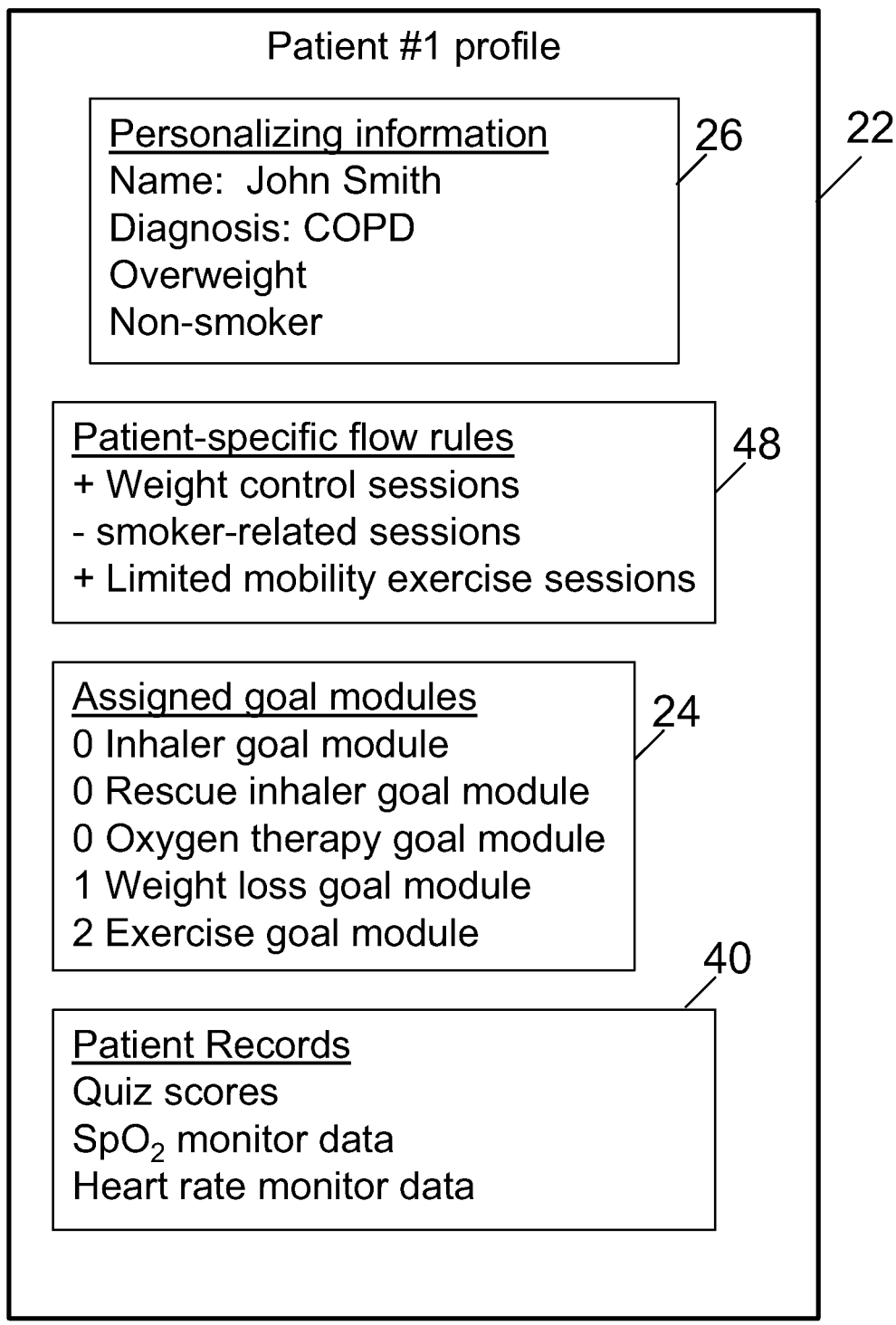

FIG. 5 diagrammatically shows content of an example patient profile.

Figure 6:
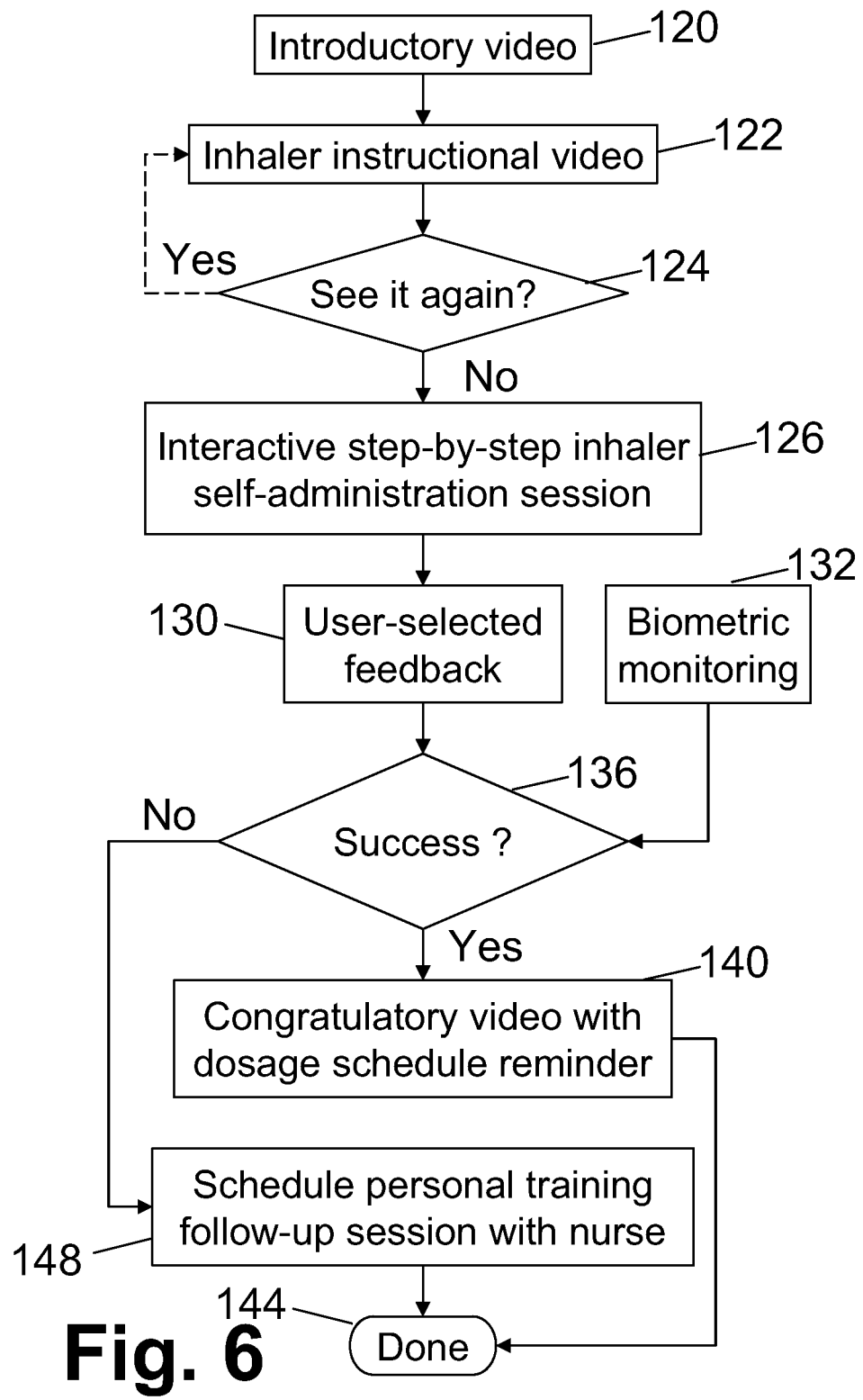

FIG. 6 diagrammatically shows content flow for an example goal module directed toward the goal of learning to self-administer an inhaled medication.

With reference to FIG. 1, a health management system 10 includes a server 12 for pushing content related to health management education, evaluation, or so forth. The content is arranged in goal modules, where each goal module includes a plurality of content sessions cooperatively directed toward achieving a health management goal. An example goal module 14 including a "Content Session #1" 16 and a "Content Session #2" 18 is shown in FIG. 1. However, it is to be appreciated that typically the server 12 includes a number of goal modules directed toward different health management goals. For example, different goal modules may be provided based on patient need or prescribed need by the clinician that are directed toward: reducing weight; stopping smoking; learning to self-administer a medical intervention such as a medication, a biometric monitor, or so forth; learning to follow a dietary restriction such as a low-salt diet; learning to follow a dietary requirement such as a high-fiber diet; performing a physical exercise; or so forth. Moreover, a typical goal module may include more than the illustrated two content sessions 16, 18. The number of content sessions in a given goal module can vary between one content session for a very simple goal module, to five, ten, or more content sessions for a complex goal module. The content sessions can include various types of content, such as: pre-recorded audio/video content; textual content; interactive survey, quiz, questionnaire, or test content; pre-recorded step-by-step interactive audio/video content; and so forth.

The health management system 10 is a goal-oriented system that pushes content related to specific health management goals that a given patient or other user is or should be striving to achieve in his or her personal health management program. To enable personalized pushing of content, each patient has an associated patient profile 22 stored on the server 12. (The term "patient" as used herein encompasses patients recovering from surgery, stroke, heart failure, or another condition, patients suffering a chronic illness that is being treated on an out-patient basis, or so forth. The term "patient" also encompasses other users of the health management system 10 who may be generally healthy but who are following a health management program assisted by the system 10 to maintain fitness, control weight, avoid osteoporosis, or otherwise maintain a healthy condition or make health-related lifestyle modifications).

The illustrated example patient profile 22 includes a list or other indication of assigned goal modules 24 that are assigned to the patient profiled by the patient profile 22. In some embodiments, the patient can only access those goal modules assigned to the patient. This arrangement can be useful for managing costs of maintaining the health management system 10, and can be useful for preventing a patient from wasting time and resources accessing irrelevant content. In other embodiments, the patient can access goal modules other than those listed in the assigned goal modules 24, but is urged to access the assigned goal modules. The patient profile 22 may optionally include other information such as personalizing information 26 that may include name, address, diagnosis, and so forth. In some embodiments, the personalizing information 26 is used to personalize content sessions. For example, a text-based content session may include name tag placeholders that are replaced by the personal name stored in the personalizing information 26 of the patient profile 22.

Although the server 12 generally operates by pushing content to the patient, the content flow is controlled or regulated by feedback from the patient or user. In the example system 10 of FIG. 1, the feedback paths include a patient user interface 30 that enables the user to provide responsive input to the server 12. Feedback provided by the user interface 30 may include answers to questions posed by the content, or answers to surveys, quizzes, tests, questionnaires, or the like that assess how well the patient or user understood previously presented content. The feedback paths also optionally include one or more biometric monitors 32 that monitor biometric parameters of the patient. Suitable biometric monitors may include, for example: a saturated blood oxygen level ($SpO_2$) monitor; a heart rate monitor; a blood pressure monitor; a weight scale; an electrocardiograph (ECG); or so forth. In a typical arrangement, the user is located at a dwelling 34 such as a house, apartment, assisted living apartment, or so forth, and does not have ready access to medical personnel. Accordingly, in some embodiments the biometric monitors 32 are advantageously designed to be simple to operate. For example, a fingertip $SpO_2$ monitor can be used to provide both saturated blood oxygen level and heart rate simply by clipping the fingertip monitor onto the patient's fingertip.

The server 12 includes a feedback module 36 that receives the responsive input via the feedback path 30, 32. Optionally, a pre-processor 38 of the server 12 may perform pre-processing of the input before using it for controlling content flow. For example, if the user provides a set of responses to a survey via the user interface 30, the pre-processor 38 may grade the responses and generate a score indicating how well the patient scored on the survey. The score is then used to control content flow, for example by showing a remedial video of the patient scored low indicating lack of comprehension. As another example, if the input includes biometric parameter measurements acquired by the biometric monitors 32 over a period of time, the pre-processor 38 may perform unit conversion, time-averaging, peak-detection, or other pre-processing of the biometric measurements. In some embodiments, some or all of the pre-processing is performed by the user interface 30 or other processor at the dwelling 34 rather than at the server 12. Optionally, the inputs provided by a patient via the user interface 30 or by the biometric monitors 32 operatively connected with the patient are stored in a patent records portion 40 of the patient profile 22.

Content is pushed to the user by a rules based content flow engine 42 that is configured to control the order of presentation of content sessions based on input received by the feedback receive module 36 and optionally pre-processed by the pre-processor 38, and further based on content flow rules. Intra-module rules 44 associated with each goal module 14 suitably govern the flow of presentation from content session to content session within the goal module 14. Optionally, inter-module rules 46 govern the flow of presentation from one goal module 14 to another goal module. For example, if the illustrated goal module 14 provides instruction for self-administering a medication that typically causes weight gain, the inter-module rules 46 associated with the goal module 14 optionally call for the content flow engine 42 to present a weight control goal module substantially concurrently with or after presentation of the goal module 14. (Substantially concurrent presentation can be achieved, for example, by interleaving presentation of content sessions of the two different goal modules.) Optionally, patient-specific flow rules 48 associated with the patient profile 22 govern content flow. For example, if the patient is a non-smoker, then the patient-specific flow rules 48 may call for omitting presentation of any sessions related to quitting smoking. Patient-specific flow rules 48 can substitute for rules 44, 46 associated with the goal module, or can supplement the goal module rules 44, 46.

Maintenance of the server 12 is suitably performed by an administrator via an administrator interface 54. The administrator may, for example, add new goal modules, delete obsolete goal modules, modify or update goal modules, modify or update content flow rules, configure the patient profile format, or so forth. The patient profile 22 is suitably maintained in accordance with a diagnosis or other information provided by the patient's doctor or other medical personnel. In some embodiments, medical personnel such as doctors or nurses can generate and/or update the patient profile 22 by directly accessing the server 12 via a medical personnel interface 56. In other embodiments, one or more system administrators perform all creation and updating of the patient profile 22 via the administrator interface 54, and in accordance with instructions from the patient's physician or other medical personnel.

Having described the illustrated components of the example health management system 10, some suitable physical implementations or layouts of the components are next described. It will be appreciated that in general, the user interface 30 can employ substantially any hardware capable of providing content presentation in unmodified and/or augmented form and capable of providing feedback to the server 12. For example, the user interface 30 can be embodied by hardware such as: a desktop computer; a laptop computer; a personal data assistant (PDA); a cellular telephone (i.e., cellphone); a television set having Internet connectivity integrally included and operated by a television remote control or other input device; a digital or analog television set having Internet connectivity provided by an add-on set-top unit and operated by a television remote control, set-top unit remote control, or other input device; or so forth. The computational components 38, 42, data storage components 14, 22, and other components 36 of the server 12 can be embodied in various ways, such as by a centralized computer or computer server, a desktop computer, or so forth. In some embodiments, existing content presentation hardware, such as an analog or digital television set, is modified or augmented by a set-top box that enables the television set to be used as a user interface for accessing the Internet or another digital network.

With reference to FIG. 2, in a relatively centralized example arrangement of components of the health management system 10, the server 12 is a centralized server that pushes content to a plurality of patients at remote locations $34_1$, $34_2$, $34_3$, and so forth. Each patient has a corresponding personalized patient profile $22_1$, $22_2$, $22_3$, and so forth. Communication between the patients and the remote centralized server 12 is achieved by a wired or wireless network connection 58. For example, the network connection 58 can be a secure high-speed wireless or wired Internet link. The network connection 58 is advantageously a secure link because private medical information may be conveyed across the network connection 58. However, unsecured connections can also be used. In some embodiments, a patient may have more than one user interface. For example, if the server 12 is accessible by a high-speed Internet connection, then the user may be able to access the server 12 via the patient's home computer, personal data assistant (PDA), Internet-enabled cellular telephone, television set having Internet connectivity integrally included and operated by a television remote control, television set having Internet connectivity provided by an add-on set-top unit and operated by a television remote control, or other Internet-capable device. If the server 12 is accessible by a cable television network, cellular telephone network, or so forth, then the user may be able to access the server 12 by a respective cable television set, cellular telephone (i.e., cellphone), interactive voice response (IVR), or so forth.

In the centralized embodiment of FIG. 2, the administrator interface 54 is suitably a network administrator account having a high level of access to a server computer embodying the server 12. The network administrator logs onto the high-level administrator account, thus enabling the administrator to add, delete, or modify the goal modules or other components of the health management system 10, modify the patient profile format, or perform other high-level tasks. On the other hand, medical personnel are optionally assigned a lower level of access through a regular user account or other network account providing lower level access. Such a lower-level account enables the doctor to access to only assigned patients. In illustrative FIG. 2, a first medical personnel interface $56_1$ corresponding to, for example, a first medical doctor's network account, enables the first doctor to access and modify patient profiles $22_1$, $22_2$ of patients who are assigned to or clients of the first doctor, but does not enable access to patient profile $22_3$ corresponding to a patient of another doctor. Conversely, a second medical personnel interface $56_2$ corresponding to, for example, a second medical doctor's network account, enables the second doctor to access and modify patient profile $22_3$ who is a patient of the second doctor, but does not enable access to patient profiles $22_1$, $22_2$ of patients who are assigned to or clients of the first doctor. In some centralized embodiments, medical personnel interfaces $56_1$, $56_2$ are omitted, and instead medical personnel provide the patient profile information to the system administrator who creates or updates the patient profiles $22_1$, $22_2$, $22_3$ via the administrator's interface 54 in accordance with instructions of medical personnel.

With reference to FIG. 3, in a relatively decentralized example arrangement of components of the health management system 10, the server 12 and the user interface 30 are embodied by a computer 60, personal data assistant (PDA), or other digital electronic device disposed at the dwelling 34 of the patient or carried with the patient or otherwise readily accessed by the patient. In these embodiments, the administrator interface 54 may include, for example, a computer at the hospital which includes an optical disk burner. The administrator, or the patient's doctor or other qualified medical personnel, loads an optical disk with the goal modules, feedback receive module software, content flow engine software, and patient profile, so as to create a personalized instance of the health management system 10 that is personalized to the specific patient. The patient then loads the contents of the personalized optical disk onto the patient's computer 60, and executes the loaded software. Rather than using an optical disk as the conduit, the personalized instance of the health management system 10 can be downloaded from a hospital computer via a cable or satellite television network, cellular telephone network, the Internet, or otherwise loaded onto the patient's computer 60, smart television, PDA, cellphone, or other device. Optionally, the administrator interface 54 may also include, for example, a secure Internet connection between a hospital computer and the patients computer 60 by which patient responses or biometric data are communicated to the doctor or hospital on a daily, weekly, or other time basis. Because in the embodiment of FIG. 3 an entire personalized instance of the health management system 10 is provided to the patient, there is typically only a single patient profile 22 corresponding to the single patient at that dwelling. It will be appreciated, however, that in the decentralized arrangement of FIG. 3, each patient will have his or her own personalized instance of the health management system 10 which will include that patient's personalized personal profile.

The centralized and decentralized arrangements or layouts of components of the health management system 10 depicted in FIGS. 2 and 3 are illustrative examples. Other arrangements can be used. For example, in some embodiments certain portions of the server 12 may reside at a centralized server computer while certain other portions of the server 12 may reside at the patient's computer. For example, the server may be located on a centralized server computer at the hospital or other centralized location and store the goal modules and patient profiles for a number of patients, but the rules-based content flow engine 42 may be an executable program downloaded to and executing on the patient's computer located at the patient's dwelling. In some embodiments, duplicate copies of portions of the server 12 or portions thereof may reside at both a centralized server computer and the patient's computer. As an example of this latter arrangement, the patient's biometric measurements may be stored at the patient's computer for ready access by the patient, and also transmitted to a centralized server computer for review by the doctor.

Having described the illustrated components of the example health management system 10 with reference to FIG. 1, and having further described some suitable physical implementations or layouts of the components with reference to FIGS. 2 and 3, operative aspects of the health management system 10 are next described.

With reference to FIG. 4, the content flow of a typical goal module presentation is described. The illustrated goal module includes four content sessions 71, 72, 73, 74. The first content session 71 is an introductory session. The second content session 72 provides training on how to use a piece of equipment needed to accomplish the health maintenance goal of the goal module. The third content session 73 provides instruction on accomplishing that medical goal. The content session 74 is a remedial equipment training session. The introductory content module 71 is presented first, and may for example present text and optional graphics or video that introduce the goal module to the patient and give the patient a preview of what is covered by the goal module. The content module 71 may also provide information that the content session 72 contains training information on the equipment used, which may be optionally skipped if the patient already knows how to use the equipment. During or after presentation of the first content session 71, the user is asked whether the patient wants to be presented with the equipment training content session 72. Based on patient feedback 75, the content flow engine 42 makes a rules based content flow decision 76 governed by flow rules 78. For example, denoting the patient feedback 75 as "ans", the flow rules 78 may then be:

IF (ans=="yes") THEN GOTO equipment training session
ELSE GOTO medical session

In accordance with these example flow rules 78, if the patient answered "yes", then content flow path 80 is followed and the patient is presented with the equipment training session 72. On the other hand, if the patient answered "no", then content flow path 82 is followed, the equipment training session 72 is skipped or omitted, and the patient is immediately presented with the medical session 73.

If the patient answered "yes" as the feedback 75, then the equipment training session 72 is presented. The equipment training session 72 may, for example, provide step-by-step interactive instruction on using the equipment. After presentation, the user is prompted for feedback 86 to determine the subsequent content flow. The feedback 86 may, for example, be answers to questions asked during the session 72. For example, the patient may have been asked during presentation of the session 72 whether certain expected results were achieved when using the equipment. If the answers were affirmative, then at a decision 88 based on flow rules 90 it may be inferred that the user has successfully learned how to use the equipment, and so content flow path 92 is followed and the patient is next presented with the medical session 73. On the other hand, if the answers were negative, then at the decision 88 based on flow rules 90 it may be inferred that the user was unsuccessful in learning how to use the equipment, and so content flow path 94 is followed and the user is presented with the remedial equipment training session 74.

Rather than basing the decision 88 on patient answers, the decision 88 may be based on direct measurement of the equipment. For example, if the equipment the patient is being trained to use is a biomedical monitor, the feedback 86 may be readings of the biometric monitor. If those readings are within an expected range, then at the decision 88 it may be inferred that the user has successfully learned how to use the equipment, and so content flow path 92 is followed and the patient is next presented with the medical session 73. On the other hand, if the readings are outside of the expected range, then at the decision 88 it may be inferred that the user was unsuccessful in learning how to use the equipment, and so content flow path 94 is followed and the user is presented with the remedial equipment training session 74.

If presented, the remedial equipment training session 74 repeats the equipment training in a slower, more detailed manner. The transition to the remedial equipment training session 74 is optionally transparent to the patient, who may perceive the content flow to remedial equipment training session 74 as a continuation of the equipment training session 72. Such a transparent transition may be useful if the patient is likely to become discouraged if told he or she requires remedial training.

The medical session 73 is reached either via the content flow path 82 that omits the equipment training, or via content flow path 92 which is followed once the patient successfully completes the equipment training session 72 and, if needed, remedial equipment training session 74. The medical session 73 provides instruction on achieving the health management goal using the equipment. For example, the medical equipment may be a heart rate monitor: equipment training sessions 72, 74 train the patient to use the heart rate monitor, while medical session 73 instructs the patient on how to monitor and regulate his or her level of exertion during exercise using the heart rate monitor. After presentation, flow path 96 is followed and the user is prompted for feedback 100 to determine the subsequent content flow. The feedback 86 may, for example, be a questionnaire, the score of which indicates how well the patient comprehended the medical instruction. If the patient gets a high enough score, then at a decision 102 based on flow rules 104 it is inferred that the user has successfully achieved the health maintenance goal of the goal module, and so content flow terminates at brief termination session 106, which may include a congratulatory or encouraging text or video message. On the other hand, if the patient's score is too low, then at the decision 102 based on flow rules 104 it may be inferred that the user has not yet achieved the health maintenance goal, and so content flow path 108 is followed which repeats the medical session 73.

FIG. 5 shows example contents of the patient profile 22 for a patient named "John Smith" whose personal information 26 a diagnosis of chronic obstructive pulmonary disease (COPD), an indication that the patient is overweight, and an indication that the patient is a non-smoker. The patient-specific flow rules 48 in FIG. 5 include:

+ Weight control sessions
− smoker-related sessions
+ Limited mobility exercise sessions where the symbol "+" indicates that sessions of this type should be included, while the symbol "−" indicates that sessions of this type should be skipped. Thus, for this overweight patient, any weight control sessions of a goal module should be presented, while for this non-smoking patient any smoker-related sessions should be omitted. In view of the debilitating nature of COPD and the overweight condition of the patient, the patient-specific flow rules 48 further specify that any exercise sessions contained in a goal module should be directed toward limited mobility exercise. This patient-specific augmentation of the flow rules can be used in various ways. In some cases, a goal module may include a plurality of exercise sessions directed toward patients of different physical condition. In these cases, the latter patient-specific flow rule specifies that the exercise session directed toward patients of limited mobility should be selected. On the other hand, in some cases, a goal module may include a single exercise session having options contained therein for patients of different physical condition. For example, the single exercise session may call for walking in place for a certain number of minutes, where the certain number of minutes is selected based on the patient's physical condition. In such a case, the patient-specific flow rule specifying limited mobility exercise sessions may be used to select a relatively low number of minutes for walking in place.

The patient profile 22 in FIG. 5 assigns the following goal modules to the patient:

0 Inhaler goal module
0 Rescue inhaler goal module
0 Oxygen therapy goal module
1 Weight loss goal module
2 Exercise goal module where the initial value provides patient-specific rules for ordering the modules. The modules denoted by the priority value "0" are most urgent and should be presented first, possibly substantially concurrently. These modules are directed toward goals that must be achieved rapidly to ensure the immediate health of the patient. On the other hand, the weight loss goal module has a priority value of "1" indicating that it is slightly less time-critical. The exercise goal module has a priority value of "2" indicating that it is still less time-critical.

With reference to FIG. 6, an example content flow for the inhaler training goal module is illustrated. A first content session provides an introductory video 120, which introduces the topic to the patient and identifies the goal to be achieved, namely learning to self-administer an inhaled medication. The introductory video content session 120 is immediately followed by an inhaler instructional video content session 122. As illustrated, there is no flow rule decision point between the introductory video content session 120 and the inhaler instructional video content session 122, since there is no alternative flow path. On the other hand, a decision point (not shown) is optionally inserted between the introduction 120 and instructional video 122 to enable the patient to opt out of the inhaler goal module if the patient decides it is not relevant or decided he or she is not ready to go through the inhaler goal module.

The instructional video 122 shows the patient how to use the inhaler in a non-interactive manner, such as by showing an actor using the inhaler. At a decision point 124 governed by suitable flow rules, the patient selects whether or not to watch the instructional video 122 again. The patient can elect to watch the instructional video 122 as many times as he or she desires, until the patient believes he or she understands the process. When the patient elects not to re-watch the video 122 again, the content flow passes to presenting an interactive step-by-step inhaler self-administration session 126. Unlike the instructional video 122, the interactive step-by-step inhaler self-administration session 126 includes step-by-step instructions and pauses during which the patient can attempt to self-medicate using his or her own inhaler medicine.

During presentation of the interactive step-by-step inhaler self-administration session 126, patient feedback is provided to the server 12. In FIG. 5, this patient feedback includes user-selected feedback 130 provided by the user interface 30, and biometric patient monitoring feedback 132 provided by the biometric monitors 32. The user-selected feedback includes answers to questions posed during the video presentation. For example, after showing how to open the mouthpiece and pausing to allow the patient to open the mouthpiece on his own inhaler, the question "Were you able to open the mouthpiece?" may be posed, and the user employs the user interface 30 to select a "yes" response or a "no" response. The biometric feedback 132 may include, for example, monitoring of respiratory rate, blood pressure, or other physiological parameters that typically exhibit a well-defined response to the inhaled medication. For example, inhalation of the medication may typically cause the respiratory rate to increase and may typically produce a rise in blood pressure. With brief reference back to FIG. 1, optionally the content flow engine 42 may automatically control the biometric monitors 32 to initiate and control acquisition of the biometric feedback 132. Alternatively, the interactive step-by-step inhaler self-administration session 126 may prompt the patient to start the biometric monitoring. Optionally, such a prompt may provide the patient with the option of transferring content flow to another goal module directed toward operating the biometric monitoring, in case the patient does not know, or has forgotten, how to operate the biometric monitors 32.

Based on the user-selected feedback 130 and the biometric feedback 132, a decision 136 is made based on content flow rules as to whether the patient successfully self-medicated using his or her inhaler. If so, then a congratulatory content session 140 is presented that congratulates the patient on his or her success, and the module terminates 144. On the other hand, if the decision 136 is that the patient was unsuccessful, then the patient is presented with an alternative content session 148 that schedules, or recommends that the patient schedule, a follow-up visit with a nurse for one-on-one training in the use of the inhaler. This recommendation of intervention of medical personnel is advantageous in that improper self-administration of inhaled medication can be dangerous to the patient and calls for rapid intervention.

An advantage of employing goal modules is that the modules can be mixed and matched based on the goals of the patient. For example, the inhaler training goal module shown in FIG. 6 may be applicable to patients having COPD, asthma, emphysema, heart failure, or other conditions that are treated using inhaled medications. Thus, the same inhaler training goal module may be assigned by the patient profiles $22_1$, $22_2$, $22_3$ to a plurality of patients having different diagnoses. Using this goal module-based approach, each goal module can be targeted narrowly toward achieving a specific narrow goal, and yet have a wide audience due to cross-diagnosis applicability, making the cost-per-patient of the goal module reasonable. Moreover, goal modules simplify maintenance of the health management system. In existing instructional videos which typically target a condition such as COPD, asthma, emphysema, heart failure, or so forth, the inhaler training may be separately included in a number of different videos. Accordingly, if a change is made in the procedure for using the inhaler (for example, because a new type of mechanical inhaler is now being used) the modifications required are extensive. In contrast, by using goal modules only the single inhaler training goal module needs to be modified.

It is to be understood that the term "goal module" encompasses a goal module directed toward the goal of maintaining an already achieved objective. That is, the goal to be achieved may be the maintenance of an already achieved objective. For example, a first goal module having as its goal achieving a 10% weight reduction may be followed by a second, maintenance goal module having as its goal maintenance of the achieved 10% weight loss. The flow rules 48 in such a case switch from the first goal module to the second, maintenance goal module when the patient reports a weight corresponding to the 10% weight loss objective.

Goal modules may optionally include optional session refresher sessions, so that the patient can selectively go back and refresh forgotten information. For example, the flow rules 48 can include selectable options for accessing refresher sessions pertaining to subject matter previously covered.

While not illustrated, the patient-specific flow rules 48 optionally include rules for sending reminders. For example, with brief reference back to FIG. 5, reminder alarms may be set up on a daily or other time-basis to display textual reminders on the television screen or other user interface until the patient accesses the critical goal modules having priority values of "0".

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A health management system comprising:
   a server configured to store (i) a plurality of goal modules, each goal module including one or more content sessions cooperatively directed toward achieving a health management goal, the health management goals of the goal modules being selected from a group consisting of: reducing weight, stopping smoking, learning to self-administer a medical intervention, learning to follow a dietary restriction, learning to follow a dietary requirement, and performing a physical exercise, the content sessions including content selected from a group consisting of: pre-recorded audio/video content, textual content, interactive survey content, and pre-recorded step-by-step interactive audio/video content, and (ii) a plurality of patient profiles, each patient profile indicating at least which goal module or goal modules are assigned to a patient profiled by the patient profile and patient-specific flow rules for that patient;

a plurality of user interfaces configured to be used by a plurality of different patients, each patient being profiled by a corresponding patient profile, each user interface including a television and a television remote, each user interface configured to present content sessions on the television and to receive at least one input via the television remote that is indicative of a user response to a content session presented by the user interface; and a content flow engine embodied by a computer and configured to control an order of presentation of content sessions based on the at least one input and on content flow rules;

wherein the content flow engine is further configured to control, for each patient, an order of presentation of goal modules assigned to the patient by the patient profile of that patient based on content flow rules including the patient-specific flow rules of the patient profile, the order of presentation of two different goal modules assigned to the patient by the patient profile being controlled by the content flow engine to be presented as one of (i) an ordered sequence or (ii) concurrently by interleaving presentation of content sessions of the two different goal modules.

2. The health management system as set forth in claim 1, wherein the at least one feedback path includes:
a survey, quiz, test, or questionnaire including at least one question presented by the television, the at least one input including a user response via the TV remote.

3. The health management system as set forth in claim 1, wherein the at least one feedback path further includes:
a biometric monitor, the at least one input including at least one biometric monitoring datum acquired by the biometric monitor.

4. The health management system as set forth in claim 1, wherein the content flow rules include a rule calling for repeating a previously presented content session responsive to a selected value or value range of the at least one input.

5. The health management system as set forth in claim 1, wherein the content flow rules include skipping at least one content session responsive to a selected value or value range of the at least one input.

6. The health management system as set forth in claim 1, wherein the content sessions include a first content session and a second remedial content session, the second remedial content session presenting subject matter of the first content session in a remedial form, the content flow rules including a rule calling for presenting the remedial second content session subsequent to the presenting of the first content session responsive to at least one input indicating inadequate comprehension of the presented first content session.

7. A health management system comprising:
a server configured to communicate with a plurality of patients, the server storing at least:

a plurality of goal modules, each goal module configured to include one or more audio/video content sessions cooperatively directed toward achieving a health management goal, a plurality of patient profiles corresponding to the plurality of patients, each patient profile configured to indicate at least which goal module or goal modules are assigned to the patient profiled by that patient profile, and a content flow engine configured to control an order of presentation of content sessions to each patient based on at least one input from the patient and on content flow rules, the rules including rules for repeating a previously presented content session, interleaving content sessions of a plurality of goal modules, and changing the order of the presentations of the content sessions, wherein the content flow rules include content flow rules stored with the goal modules and at least some patient-specific content flow rules stored in the patient profiles; and for each patient, a patient-accessible apparatus configured to communicate with the server to provide health management content to a patient profiled on the server, the patient-accessible apparatus including:
a television set accessible by the patent and configured for presenting content sessions pushed to the television set by the server, and
a television remote control accessible by the patient and configured to provide the at least one input from the patient to the server;
wherein the order of presentation via the patient-accessible apparatus of two different goal modules assigned by the patient profile corresponding to the patient is controlled by the content flow engine to be presented as one of (i) an ordered sequence or (ii) concurrently by interleaving presentation of content sessions of the two different goal modules.

8. The health management system as set forth in claim 7, wherein the content flow engine is configured to present at least one of a survey, quiz, test, and questionnaire to solicit the at least one input from the patient.

9. The health management system as set forth in claim 7, wherein the plurality of patient profiles further assign a medical diagnosis to each patient, the plurality of patient profiles assigning the same goal module to at least two different patients having different diagnoses.

10. A modular health management system comprising:
a server configured to communicate with a plurality of patients, the server storing at least:
a plurality of goal modules, each goal module configured to include one or more content sessions cooperatively directed toward achieving a health management goal, and
a plurality of patient profiles corresponding to the plurality of patients, each patient profile being modularly constructed by assigning selected goal modules configured for presentation to the patient profiled by that patient profile and patient-specific content flow rules configured to control flow of presentation of the selected goal modules for the patient profiled by the patient profile, wherein at least one of the plurality of goal modules is shared amongst two or more different patient profiles, and
content flow rules configured to control an order of presentation of the content sessions the content flow rules including:

intra-module rules associated with a goal module configured to control a flow of presentation from content session to content session within the goal module, and inter-module rules configured to control a flow of presentation from one goal module to another goal module, an electronic user interface for each profiled patient including a display and at least one user input device, the electronic user interface configured to present the patient with the selected goal modules assigned to that patient by the patient profile and to receive feedback from the patient responsive to the presentation; and a content flow engine embodied by a computer and configured to, for each profiled patient:

control the order of presentation of two different goal modules assigned by the patient profile to be presented as one of (i) an ordered sequence or (ii) concurrently by interleaving presentation of content sessions of the two different coal modules, and change the order of presentation of content sessions based on the patient feedback and the content flow rules including the intra-module rules, the inter-module rules, and the patient-specific content flow rules of the patient profile.

\* \* \* \* \*